US010632777B2

(12) United States Patent
Ikeda et al.

(10) Patent No.: US 10,632,777 B2
(45) Date of Patent: Apr. 28, 2020

(54) WATER PRESSURE TRANSFER METHOD AND WATER PRESSURE TRANSFER FILM

(71) Applicant: TAICA CORPORATION, Tokyo (JP)

(72) Inventors: Wataru Ikeda, Shizuoka (JP); Akiko Yamazaki, Shizuoka (JP); Kazutoshi Toda, Shizuoka (JP); Takahiro Sasazawa, Kakegawa (JP)

(73) Assignee: TAICA CORPORATION, Tokyo (JP)

( * ) Notice: Subject to any disclaimer, the term of this patent is extended or adjusted under 35 U.S.C. 154(b) by 334 days.

(21) Appl. No.: 15/531,899

(22) PCT Filed: Nov. 30, 2015

(86) PCT No.: PCT/JP2015/083540
§ 371 (c)(1),
(2) Date: May 31, 2017

(87) PCT Pub. No.: WO2016/088702
PCT Pub. Date: Jun. 9, 2016

(65) Prior Publication Data
US 2017/0267006 A1 Sep. 21, 2017

(30) Foreign Application Priority Data

Dec. 1, 2014 (JP) .................................. 2014-242825

(51) Int. Cl.
B41M 3/12 (2006.01)
B41F 16/00 (2006.01)
(Continued)

(52) U.S. Cl.
CPC ................. B41M 3/12 (2013.01); B32B 7/06 (2013.01); B32B 7/12 (2013.01); B32B 23/06 (2013.01);
(Continued)

(58) Field of Classification Search
CPC .... A61K 31/198; A61K 31/21; A61K 31/505; A61K 31/52; B44C 1/175; B44C 1/1758;
(Continued)

(56) References Cited

U.S. PATENT DOCUMENTS 2,271,413 A * 1/1942 Braverman ........... B44C 1/1733
428/205
4,231,829 A * 11/1980 Marui .................... B41M 5/025
156/230
(Continued)

FOREIGN PATENT DOCUMENTS

JP 63094900 A 4/1988
JP 01022378 A 1/1989
(Continued)

Primary Examiner — Sonya M Sengupta
(74) Attorney, Agent, or Firm — Pearne & Gordon LLP

(57) ABSTRACT

When water pressure transfer of decorative layer or layers is carried out on an article using a water pressure transfer sheet 202 having a non-extensible decorative layer 22 providing hologram function and an extensible decorative layer 24 of print pattern sequentially from a top of said water pressure transfer sheet, a plurality of preformed cracks 26 are formed in said non-extensible decorative layer 22 of said water pressure transfer sheet 201 before said water pressure transfer sheet 202 lands on water, then an activating agent for wetting and activating said extensible decorative layer 24 is applied, and thereafter said water pressure transfer sheet lands on the water whereby water pressure transfer is carried out having high profile followability.

19 Claims, 9 Drawing Sheets

(51) Int. Cl.

| | |
|---|---|
| *B32B 27/00* | (2006.01) |
| *B44C 1/175* | (2006.01) |
| *B32B 23/06* | (2006.01) |
| *B32B 7/12* | (2006.01) |
| *B32B 29/08* | (2006.01) |
| *B32B 23/08* | (2006.01) |
| *B32B 7/06* | (2019.01) |
| *B32B 27/10* | (2006.01) |
| *B32B 27/28* | (2006.01) |
| *B32B 27/08* | (2006.01) |
| *B32B 27/30* | (2006.01) |
| *B41M 1/40* | (2006.01) |
| *A61K 31/21* | (2006.01) |
| *A61K 31/52* | (2006.01) |
| *A61K 31/198* | (2006.01) |
| *A61K 31/505* | (2006.01) |

(52) U.S. Cl.
CPC ............ *B32B 23/08* (2013.01); *B32B 27/00* (2013.01); *B32B 27/08* (2013.01); *B32B 27/10* (2013.01); *B32B 27/28* (2013.01); *B32B 27/302* (2013.01); *B32B 29/08* (2013.01); *B41F 16/00* (2013.01); *B41M 1/40* (2013.01); *B44C 1/175* (2013.01); *B44C 1/1758* (2013.01); *A61K 31/198* (2013.01); *A61K 31/21* (2013.01); *A61K 31/505* (2013.01); *A61K 31/52* (2013.01); *B32B 2255/10* (2013.01); *B32B 2255/205* (2013.01); *B32B 2255/28* (2013.01); *B32B 2307/20* (2013.01); *B32B 2307/402* (2013.01); *B32B 2307/412* (2013.01); *B32B 2307/422* (2013.01); *B32B 2451/00* (2013.01)

(58) Field of Classification Search
CPC . B41M 1/40; B41M 3/12; B41F 16/00; B32B 27/00; B32B 23/06; B32B 7/12; B32B 29/08; B32B 23/08; B32B 7/06; B32B 27/10; B32B 27/28; B32B 27/302; B32B 2307/402; B32B 2307/422; B32B 2451/00; B32B 2307/412; B32B 2255/205; B32B 2255/28; B32B 2307/20; B32B 2255/10
USPC .................................. 156/247, 249, 703, 706
See application file for complete search history.

(56) References Cited

U.S. PATENT DOCUMENTS 4,337,289 A * 6/1982 Reed .................. B41M 3/12
428/211.1
2015/0322561 A1  11/2015  Cai

FOREIGN PATENT DOCUMENTS

| | | |
|---|---|---|
| JP | 03156000 A | 7/1991 |
| JP | 2001328398 A | 11/2001 |
| JP | 2006051672 A | 2/2006 |
| JP | 2009241613 A | 10/2009 |
| JP | 2013000893 A | 1/2013 |
| JP | 2013000894 A | 1/2013 |
| JP | 2013000896 A | 1/2013 |
| JP | 2013000897 A | 1/2013 |
| JP | 2013067096 A | 4/2013 |
| JP | 2013067097 A | 4/2013 |
| JP | 2013071322 A | 4/2013 |
| WO | 2014079097 A1 | 5/2014 |
| WO | 2014157316 A1 | 10/2014 |

* cited by examiner

Fig. 2
(A)
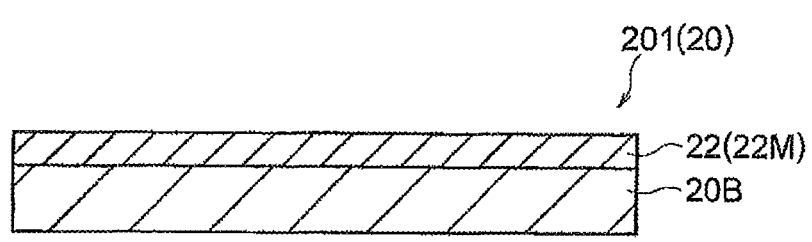
(B)
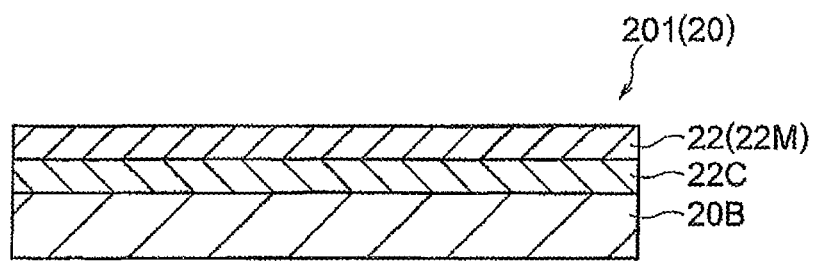

Fig.12
(A)
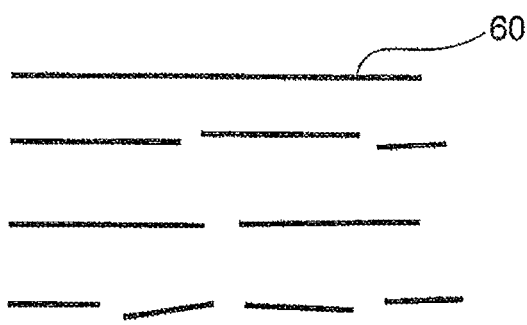
(B)
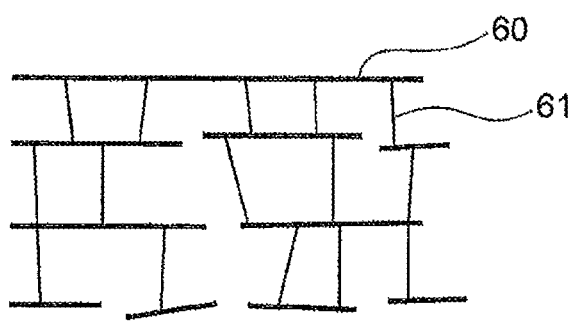
(C)
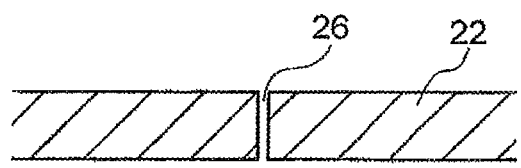
(D)
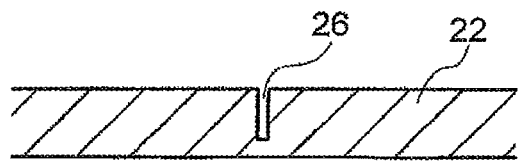

WATER PRESSURE TRANSFER METHOD AND WATER PRESSURE TRANSFER FILM

TECHNICAL FIELD

This invention relates to a method of carrying out water pressure transfer using water pressure transfer sheet having a decorative layer (transfer layer) providing a functionality including photoluminescence such as metal tone, plating tone, hologram tone or the likes and water pressure transfer sheet to be used for this method.

BACKGROUND OF THE INVENTION

Of late, in technology decorating a surface of an article, there has been drawn attention to technology providing the functionality including photoluminescence obtained by formation of a thin film of metal or metal oxide, etc., UV protection, photo-catalyst function, electric conductivity, etc., in addition to or in replacement of a decoration based on printing or painting by conventional pigment-type or dye-type ink.

Especially, in order to obtain an advanced design, a demand of photoluminescent designs like metal tone, color plating tone or hologram tone has increased and there has been conventionally practiced a decorative technology in which such photoluminescent designs have been provided by spatter-processing articles.

However, in case where the designs are to be expressed in combination with the decorative layer by the conventional printing or painting, the decoration technology by the spatter-processing requires separate printing or painting step before or after the spattering step, which takes much time to thereby have poor workability.

In order to improve the decoration technology for providing photoluminescence by such two processes, there has been proposed water pressure transfer sheet (sometimes referred to as water pressure transfer film) used for obtaining a photoluminescent decorative layer by water pressure transfer (see Patent documents 1 to 6). Among them, all of the water pressure transfer sheets of the Patent documents 1 to 3 comprise water-soluble base substance film (Carrier film) and a metal layer formed on the water-soluble base substance film by vapor deposition directly or through a resin layer. Moreover, all of the water pressure transfer sheets of the Patent documents 4 to 6 comprise water-soluble base substance film (carrier film), a transparent resin layer formed on the water-soluble base substance film and a metal layer formed by vapor deposition or sputtering on the transparent resin layer and the metal layer and/or the transparent resin layer are embossed if needed. If the water pressure transfer is carried out on an article by using the water pressure transfer sheets of these Patent documents, a decorative layer having a hologram effect will be formed on the article. However, since the metal layer of the water pressure transfer sheet never swell by water, the metal layer has poor profile followability (attachment followability) relative to the three-dimensional surface of the article to be decorated by the water pressure transfer and therefore there have been a problem of being not able to manufacture a decorated article of high quality. Furthermore, although, in some case, the water pressure transfer sheet may be extended by cracks occurring in the metal layer by tensile stress generated when the water-soluble base substrate film swells and is expanded by water, even in this case, the cracks become uneven depending on the affinity with the extension characteristics of the resin layer and therefore, there occurs a problem of deteriorating the effect of the design.

In order to solve such a problem, there has been proposed water pressure transfer film having water-wettable transfer control layer between an embossed metal layer and water-soluble base substance film (see the Patent documents 7 to 12). Since the uniformity of the cracks formed in the metal layer is improved by the transfer control layer when the water pressure transfer film is expanded, the transfer film has the improvement on the followability to the three-dimensional surface of the article and the effect of the design. However, since the generated pattern of the cracks of the metal layer changes according to a pitch and a depth of the emboss (unevenness), if the uniformity of the cracks tries to be realized by controlling the pitch and the depth of the emboss, the freedom of design in the effect of the design (the hologram effect etc., for example) of photoluminescence resulting from embossing may be often restricted and it is required that this should be improved.

Although similar to the layer composition of the Patent document 7, there has been proposed a transfer film having no embossing composition (see the Patent document 13). Using the transfer film of such composition, the above problem resulting from the embossing will be able to be solved, but in case where the decorative layer of the water pressure transfer sheet has an additional print layer under the metal layer, even though an activating agent tries to be applied in order to activate the dried print layer to restore adhesiveness and/or swelling of the print layer, the metal layer prevents the activating agent from permeating the print layer. Thus, since the print layer is never wetted to thereby prevent the extension of the water pressure transfer sheet, the extensibility of the water pressure transfer film and the formation of the cracks in the metal layer become unstable and therefore there has been a problem of defect occurred regarding the followability of the decorative layer to the surface of the article (attachment followability or the effect of water pressure transfer) and the effect of the design. This problem similarly occurs in the conventional method disclosed in the Patent documents 7 through 12.

Furthermore, Since the extensibility of the water pressure transfer sheet is determined on the conditions of formation of the water-soluble base substrate film and the metal layer, the conditions where the action of extension of the water pressure transfer sheet during the water pressure transfer process is adjusted becomes restrictive. Thus, it is required to improve the producibility in view of this aspect.

PRIOR ART LITERATURE

Patent Document

Patent document 1: Unexamined Patent Publication JP 1988 (Showa 63)-094900
Patent document 2: Unexamined Patent Publication JP 1991 (Heisei 03)-156000
Patent document 3: Unexamined Patent Publication JP 1989 (Heisei 01)-022378
Patent document 4: Unexamined Patent Publication JP 2001-328398 (U.S. Pat. No. 4,382,964)
Patent document 5: Unexamined Patent Publication JP 2009-241613 (U.S. Pat. No. 5,075,887)
Patent document 6: WO2014/079097
Patent document 7: Unexamined Patent Publication JP 2013-000893
Patent document 8: Unexamined Patent Publication JP 2013-000896

Patent document 9: Unexamined Patent Publication JP 2013-000897
Patent document 10: Unexamined Patent Publication JP 2013-067096
Patent document 11: Unexamined Patent Publication JP 2013-067097
Patent document 12: Unexamined Patent Publication JP 2013-071322
Patent document 1.3: Unexamined Patent Publication JP 2013-000894

SUMMARY OF THE INVENTION

Problem to be Solved by the Invention

The problem to be solved by the invention is to provide a method for carrying out water pressure transfer in which a uniform extension of water pressure transfer sheet having a non-extendable decorative layer of metal or metal oxide, etc. being not wetted by water or an activating agent (referred to as "non-extendable decorative layer later) is carried out without any use of special extendibility control layer and therefore water pressure transfer is carried out while the attachment followability of the decorative layer to a surface of an article and the functionality such as photoluminescence are improved.

Another problem to be solved by the invention is to provide a method for carrying out water pressure transfer in which a uniform extension of water pressure transfer sheet having a non-extendable decorative layer and an extendable decorative layer such as a print layer extendable and deformable by being dissolved or softened by an activating agent (referred to as "extendable decorative layer" later) can be carried out to positively perform an activation of the print layer of the extendable decorative layer and therefore water pressure transfer can be carried out while the attachment followability of the decorative layer to a surface of an article and the functionality such as photoluminescence are improved.

A further problem to be solved by the invention is to provide water pressure transfer sheet suitable for water pressure transfer in which a uniform extension of water pressure transfer sheet having a non-extendable decorative layer can be carried out and therefore water pressure transfer can be carried out while the attachment followability of the decorative layer to a surface of an article and the functionality such as photoluminescence are improved.

A further problem to be solved by the invention is to provide water pressure transfer sheet suitable for water pressure transfer in which a uniform extension of water pressure transfer sheet having a non-extendable decorative layer and an extendable decorative layer can be carried out while an activation of the extendable decorative layer is positively performed and therefore water pressure transfer can be carried out while the attachment followability of the decorative layer to a surface of an article and the functionality such as photoluminescence are improved.

A first problem solution means according to the invention is to provide water pressure transfer method comprising the steps of disposing on water surface of water pressure transfer tub water pressure transfer sheet comprising water-soluble base substrate film and a transfer layer including at least a non-extendable decorative layer formed on said water-soluble base substrate layer and forcing an article against said water pressure transfer sheet whereby said transfer layer is transferred onto a surface of said article, characterized in that said non-extendable decorative layer of said water pressure transfer sheet has a plurality of preformed cracks in the direction of thickness before said water pressure transfer sheet lands on said water surface.

In the first problem solution means, at least portions of said preformed cracks preferably extend through said non-extendable decorative layer in the direction of thickness.

In the first problem solution means, in case where the expansion rates at the time of swelling of the water-soluble base substance film of the water pressure transfer sheet vary based on the orthogonal directions of the water pressure transfer sheet, respectively, the plurality of aforementioned preformed cracks are preferably formed along the direction of larger expansion rate. In case where the water pressure transfer method is in the form of continuous water pressure transfer using the water pressure transfer sheet having the expansion rate of widthwise direction larger than that of the longitudinal (advancing) direction, the plurality of preformed cracks are preferably formed along the widthwise direction of the water pressure transfer sheet (water-soluble base substance film).

In the first problem solution means of the present invention, in case where the transfer layer includes extensible decorative layer, the plurality of preformed cracks may be formed before an activating agent is applied onto the water pressure transfer sheet, and in this case, the plurality of preformed cracks may be formed in advance at the manufacturing of the water pressure transfer sheet. On the other hand, in case where the water pressure transfer sheet includes only a non-extensible decorative layer, the plurality of preformed cracks may be formed before adhesives are applied onto the water pressure transfer sheet, and in this case, the plurality of preformed cracks may be formed in advance at the time of manufacture of the water pressure transfer sheet. Furthermore, even in case where the transfer layer includes the extensible decorative layer or even in case where the transfer layer includes no extensible decorative layer, the plurality of preformed cracks may be formed before the water pressure transfer sheet lands on the water surface after it is fed from the supply source thereof.

In the first problem solution means of the present invention, the water pressure transfer may be carried out by extending the water pressure transfer sheet to a state where the extension force disappears and thereafter gradually and forcibly reducing the water pressure transfer sheet in the widthwise direction until it becomes the state of predetermined reduced width.

In the first problem solution means of the invention, the non-extensible decorative layer may be a metal layer or a metal oxide layer and at least the non-extensible decorative layer may be embossed.

In the first problem solution means of the invention, the activating agent or the adhesives may be applied at the time when the water pressure transfer sheet lands on the water surface and the water-soluble base substance film begins to swell.

The second problem solution means of the invention is to provide water pressure transfer sheet having a transfer layer including water-soluble base substance film and at least a non-extensible decorative layer formed on the water-soluble base substance film, characterized in that the non-extensible decorative layer has a plurality of preformed cracks in the direction of thickness.

In the second problem solution means of the invention, it is desirable that at least parts of the plurality of preformed cracks penetrate through the non-extensible decorative layer in the thickness direction thereof.

In the second problem solution means of the invention, it is desirable that the water pressure transfer sheet has expansion rates different on its orthogonal directions at the time of swelling, respectively and that the plurality of preformed cracks are formed along the direction in which the expansion rate is larger. In this case, the plurality of preformed cracks are formed along the widthwise direction of the water pressure transfer sheet so that the expansion rate of the widthwise direction of the water pressure transfer sheet may become larger than the expansion rate of the longitudinal direction (advancing direction) thereof.

In the second problem solution means of the invention, the water pressure transfer sheet may include a dried extensible print layer under the non-extensible decorative layer. The non-extensible decorative layer may be a metal layer or a metal oxide layer.

Furthermore, in the second problem solution means of the invention, a least the non-extensible decorative layer may be embossed.

Effect of the Invention

According to the present invention, the plurality of cracks are formed in the non-extensible decorative layer of the water pressure transfer sheet (intentionally) beforehand before the water pressure transfer sheet lands on the water surface and since these preformed cracks can be formed on the appropriately controlled conditions when the water pressure transfer sheet is manufactured or before the water pressure transfer sheet lands on the water surface, there is never imparted to the water-soluble base substance film an irregular extensibility causing the cracks to be spontaneously and unstably generated in the non-elastic decorative layer after the water pressure transfer sheet lands on the water surface as in the conventional art. Thus, the extensibility of the non-extensible decorative layer of the water pressure transfer sheet (the formation action of the crack spontaneously generated by tensile stress when the water-soluble film swells) can be adjusted on the basis of the preformed cracks and therefore the water pressure transfer can be carried out on the surface of article with high productivity in the state where the followability (attachment followability) of the decorative layer to the surface of the article and the functionality of the decorative layer are stabilized.

Furthermore, in case where the water pressure transfer sheet has the extensible decorative layer such as the dried print layer under the non-extensible decorative layer, since the activating agent for activating the extensible decorative layer is permeated through the cracks previously formed before the application of the activating agent to be able to activate the decorative layer, the stable extensibility can be imparted to the whole water pressure transfer sheet by the controlled preformed cracks in the non-extensible decorative layer and the permeation of the activating agent into the print layer and therefore the good attachment followability can be obtained with the result that the decorated article of excellent functional design can be provided in a stable manner.

BRIEF DESCRIPTION OF THE DRAWINGS

FIG. 2 illustrates the first form of the water pressure transfer sheet used for the method of the invention, wherein FIG. 2A is a vertical sectional view of the water pressure transfer sheet having a non-extensible decorative layer, but not an extensible decorative layer, FIG. 2B is a vertical sectional view of the water pressure transfer sheet additionally including a transparent resin layer to the water pressure transfer sheet of FIG. 2A;

FIG. 3 illustrates the second form of the water pressure transfer sheet used for the method of the invention, wherein FIG. 3A is a vertical sectional view of the water pressure transfer sheet having a non-extensible decorative layer and an extensible decorative layer sequentially shown from top to bottom, FIG. 3B through 3D are vertical sectional views of the water pressure transfer sheet embossed in different modes in the water pressure transfer sheet of FIG. 3 (A) and FIG. 3E is substantially identical to FIG. 3D, but a vertical sectional view of the water pressure transfer sheet for imparting typical hologram function in the desirable form having an extensible decorative layer comprising two layer portions and FIG. 3F is a vertical sectional views of the water pressure transfer sheet having an extensible decorative layer, a non-extensible decorative layer and a transparent resin layer sequentially shown from top to bottom;

FIG. 12 is a schematic diagram of the forms of the preformed cracks formed in the non-extensible decorative layer of the water pressure transfer sheet of the invention wherein FIGS. 12A and 12B are plane views of the preformed cracks in the different forms and FIGS. 120 and 12D are enlarged vertical sectional views of the decorative layers having the preformed cracks of totally extension-through and of no extension-through, respectively.

MODE OF EMBODYING THE INVENTION

Figure 1:
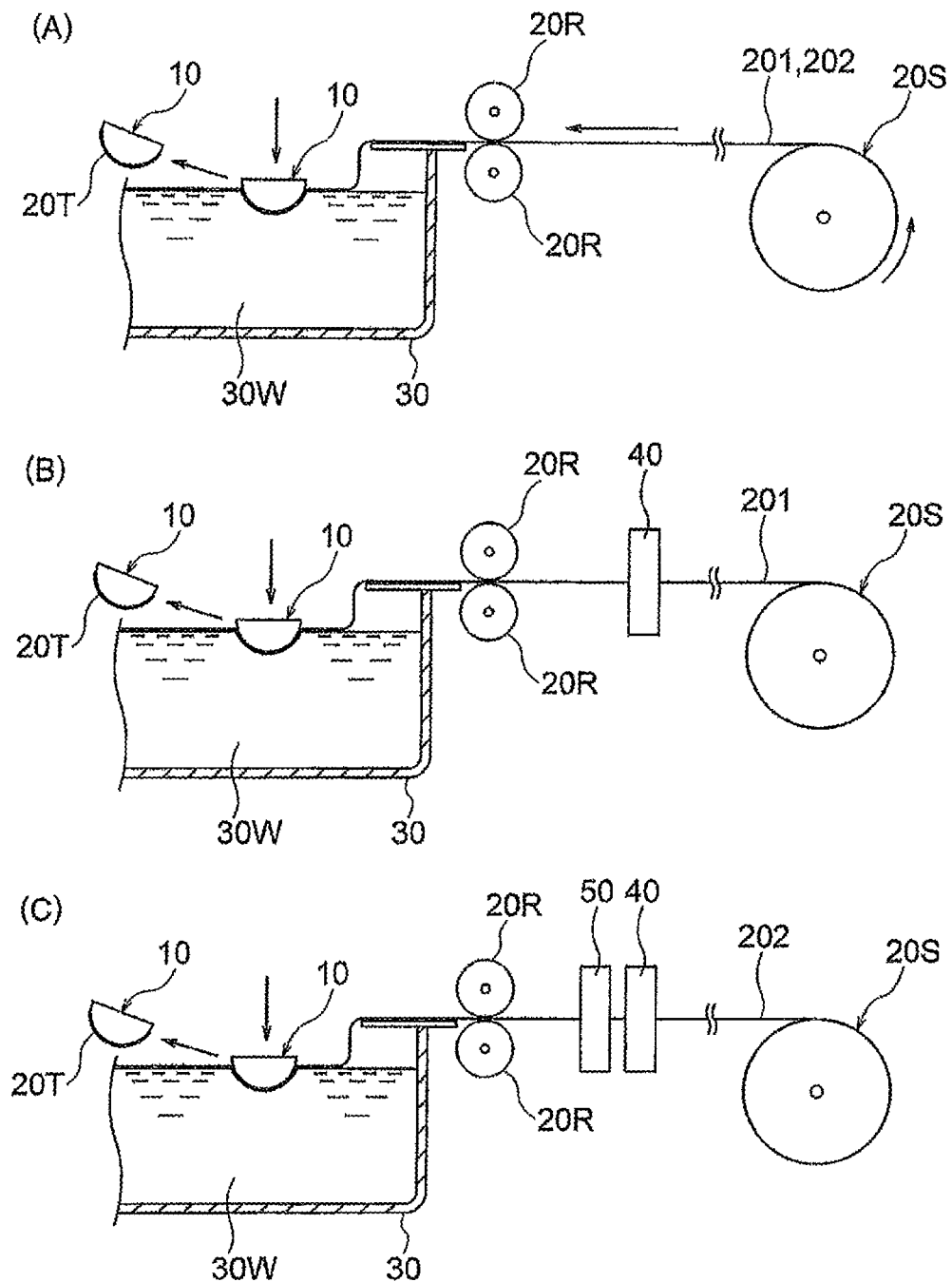
FIG. 1 is a summary diagram of water pressure transfer method in the different forms in which the method of the invention is applied.

Describing the water pressure transfer method of the invention in details with reference to the drawings, the invention relates to a method in which water pressure transfer sheet 201 (see FIG. 2) having a non-extensible decorative layer 22 never swelling or expanding due to water or an activating agent, but having no extensible decorative layer swelling and expanding due to the water or the activating agent or water pressure transfer sheet 202 (see FIG. 3) having a non-extensible decorative layer 22 and an extensible decorative layer 24 is fed out from a source of supply 20S through a supply roll 20R, is forced into water 30W within a water pressure transfer tub together with an article 10 whereby the decorative layer 22 or the decorative layers 22 and 24 of the water pressure transfer sheet 20 (generically referred to as a numeral 20 for the water pressure transfer sheets 201 and 202 hereafter) are transferred on the surface of the article 10 under water pressure to form a transfer layer 20T. Before or after the water pressure transfer sheet lands on the water surface, a proper adhesive may be applied onto the water pressure transfer sheet 201 for adhering the non-extensible decorative layer 22 onto the article while before or after the water pressure transfer sheet lands on the water surface, a proper activating agent may be applied onto the water pressure transfer sheet 202 for wetting the extensible decorative layer 24 to adhere the decorative layer 24 onto the article or for wetting the extensible decorative layer 24 to restore the extension property of the extensible decorative layer 24 (see FIG. 3F). In case where the non-extensible decorative layer 22 is disposed on the top of the water pressure transfer sheet, it is required that the activating agent contains an adhesive ingredient which adheres the non-extensible decorative layer 22 on the article 10.

The water-soluble base substance film (carrier film) 20B of the water pressure transfer sheet 20 is formed of water-soluble material having a main component of polyvinyl alcohol, for example, which absorbs water and swells to be softened and expanded. When the water pressure transfer is carried out, the water-soluble base substance film 20B contacts the water 30W within the transfer tub to be softened and attaches the periphery of the article whereby the water pressure transfer can be carried out.

As explained later, the non-extensible decorative layer 22 of the water pressure transfer sheet 20 is the decorative layer to be hard to be expanded on the water pressure transfer because of having no property to be wetted by water and softened by the activating agent by water such as the layer of metal or metal oxide and the non-extensible decorative layer 22 may be formed by appropriate means such as vapor deposition and sputtering on the water-soluble base substance film (carrier film) 20B, which is shown in FIGS. 2A and 2B. The extensible decorative layer 24 of the water pressure transfer sheet 20 is the decorative layer such as the print layer of pattern formed by ink or paint which dissolves or softens by means of the activating agent to be expanded on the water pressure transfer, which will be explained later. The extensible decorative layer 24 may be formed by appropriate printing means such as gravure printing or others on the water-soluble base substance film (carrier film) 20B as shown in FIGS. 3(A) through 3(E) while the non-extensible decorative layer 22 of the water pressure transfer sheet 202 may be formed by appropriate means such as vapor deposition or sputtering on the extensible decorative layer 24. The water pressure transfer sheet 202 of FIGS. 3(B) though 3(E) is embossed in parts or all of the layers. The water pressure transfer sheet 202 of FIG. 3 (F) is identical to the water pressure transfer sheet 202 of FIG. 3(A), except that the water pressure transfer sheet 202 of FIG. 3(F) has the extensible decorative layer 24 formed not under the non-extensible decorative layer 22, but on the non-extensible decorative layer 22 and the transparent resin layer 22C is formed between the water-soluble base substance film 20B and the non-extensible decorative layer 22. Of course, the water pressure transfer sheet 202 of FIG. 3 (F) may be embossed as in FIGS. 3(B) through 3 (E).

Typically, the non-extensible decorative layer 22 may comprise a metal layer 22M of metal or metal oxide formed by vapor deposition or sputtering and having photoluminescence imparting function. Of course, this non-extensible decorative layer 22 may be a transfer layer providing the functionality such as UV protection, photocatalyst function, conductivity, electromagnetic wave absorption etc., for example in replacement of or in addition to the function of design property like the photoluminescence imparting function. The non-extensible metal layer 22M providing the photoluminescence function may be formed of metal alone such as aluminum, chromium, nickel, copper, gold, tin, zinc, brass and stainless steel or an alloy thereof or metal oxide such as aluminum oxide and silica dioxide, for example. The thickness of the metal layer 22M may be 10-80 nm and more preferably 20-60 nm in case where it is formed of metal alone and preferably 10-300 nm in the case where light is emitted by metal oxide. In the water pressure transfer sheet 201 of FIG. 2 (B), there is provided the transparent resin layer 22C between the water-soluble base substance film 20B and the non-extensible decorative layer 22 and the transparent resin layer 22C has such a function as the non-extensible decorative layer 22 can be stably formed on the water-soluble base substance film 20B. The transparent resin layer 22C is such a layer as the extensibility is imparted by the water or the activating agent and may be formed of nitro-cellulose type resin or Alkyd type resin, etc., for example.

Figure 3:
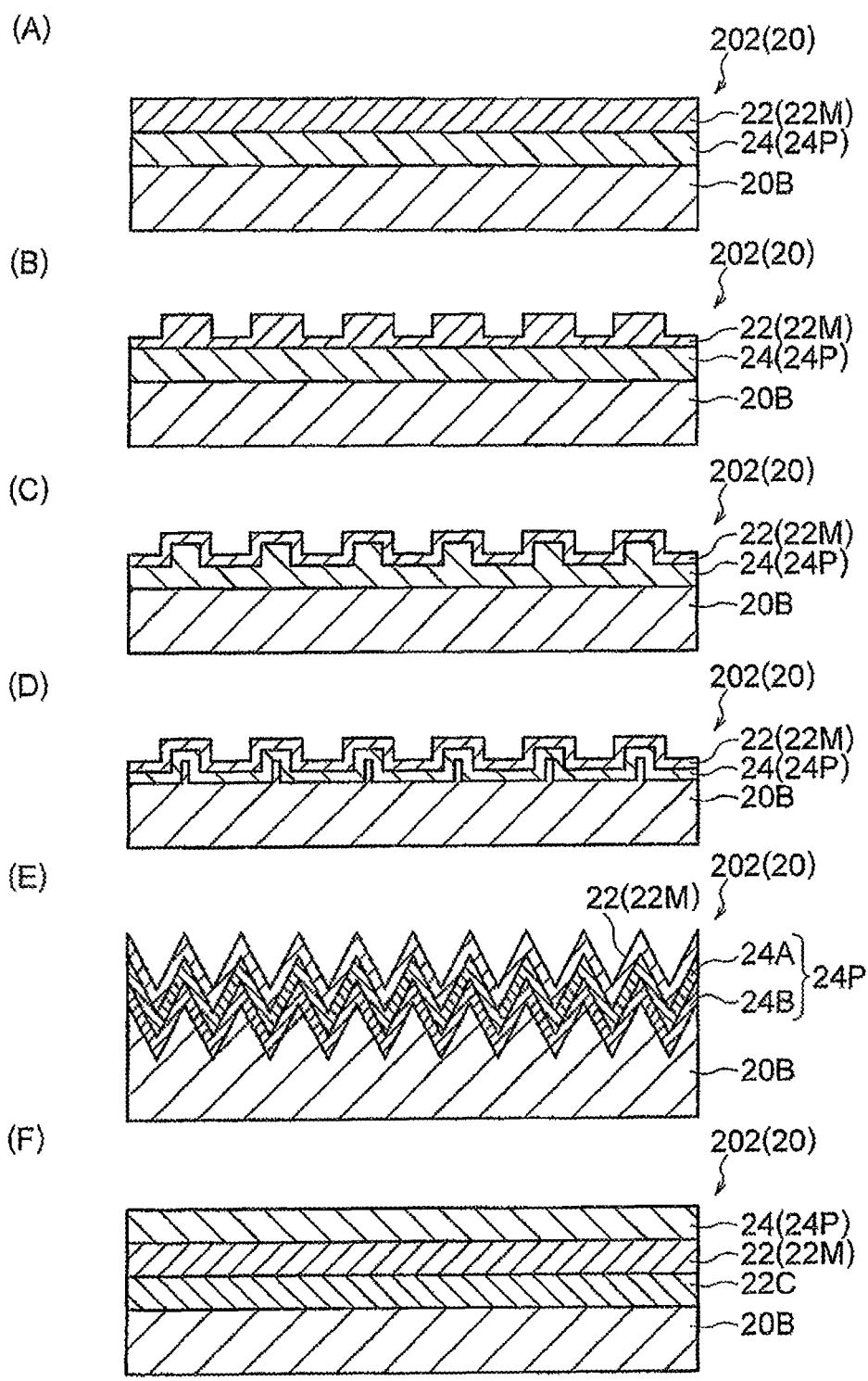

The extensible decorative layer 24 of the water pressure transfer sheet 202 may comprises the print layer 24P providing patterns or colors to an article 10 and the print layer 24P is in the form of being dried for the purpose of storage of the water pressure transfer sheet until an activating agent is applied thereto and it is dissolved or softened to recover its adhesiveness and be easily extended by the activating agent after the activating agent is applied thereon. The ink used for a print layer may be the same as what is used for the conventional water pressure transfer sheet. The print layer 24P may be a print layer of plain form (non-pattern) other than patterns, characters or signs. As shown in FIG. 3(E), the extensible decorative layer 24 may be formed of a plurality of layer portions. Moreover, the extensible decorative layer 24 may be laminated onto the lower face of the non-extensible decorative layer 22 (on the side of the water-soluble base substance film) as shown in FIGS. 3(A) through 3(D) or onto the upper face of the non-extensible decorative layer 22 as shown in FIG. 3 (F). In any form of the lamination after the water pressure transfer, the decorative layer(s) on the lower side can be sawn through from the decorative layer(s) on the lower side after the water pressure transfer or otherwise, the lower decorative layer may be partially exposed so that both of the non-extensible decorative layer 22 and the extensible decorative layer 24 can be viewed at least partially after the water pressure transfer.

As shown in FIG. 3(B) through FIG. 3 (D), the water pressure transfer sheet 202 may have the layer or layers of the sheet embossed by using a conventional method for providing a hologram function. This emboss processing should just provide a concavo-convex form which can produce the diffraction phenomena of light and the depth of this emboss may be 0.02-2 micrometers while the periodic width (pitch) may be 0.5-2 micrometers. Herein, what is meant by the periodic width (pitch) is a spaced distance between the adjacent convex parts (the distance between the centers of the adjacent convex part). The emboss-processing may be carried out to each of the non-extensible decorative layer 22 and the extensible decorative layer 24 or both of them. Furthermore, although not illustrated in FIG. 3, the water-soluble base substance film may be embossed.

Figure 10:
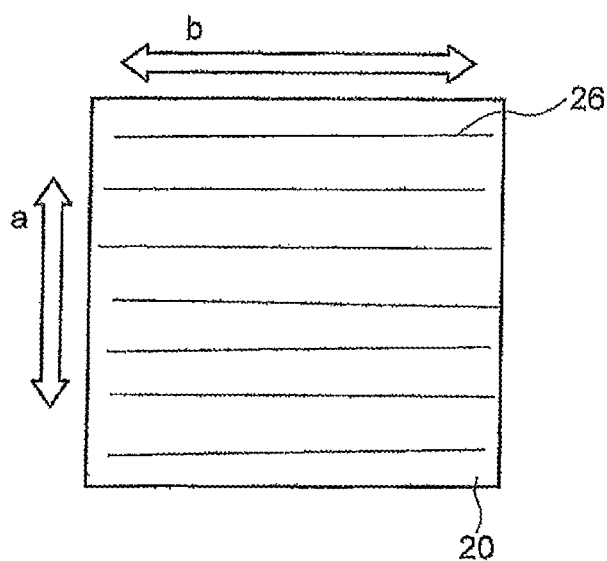
FIG. 10 is a plane view partially showing water pressure transfer sheet used for the invention.

When the principle of the invention is that for a purpose of improvement on the uniformization of the swelling extensibility of the water pressure transfer sheet 20 and the attachment followability thereof to the article when the water pressure transfer of the decorative layers 22 and 24 carried out to the article using the water pressure transfer sheet 20 having only the non-extensible decorative layer 22 or both of the non-extensible decorative layer 22 and the extensible decorative layer 24, a plurality of cracks 26 (referred to as preformed cracks later and explained in detail with reference to FIG. 10 and FIG. 12 later) are formed in the non-extensible decorative layer 22 before the water pressure transfer sheet 20 lands on the water to thereby uniformize the cracks spontaneously formed in the non-extensible decorative layer 22 by a swelling expansion force of the water-soluble base substance film 20B after the water pressure transfer sheet 20 lands on the water (referred to as swelling expansion cracks later) and to adjust the formation action of the swelling expansion cracks according to the form of the preformed cracks 26 whereby the swelling expansion and the attachment followability can be provided to the water pressure transfer sheet 20. The preformed cracks 26 may be formed in the water pressure transfer sheet 20 during the production of the water pressure transfer sheet 20 or before the water pressure transfer sheet 20 lands on the water. Herein, explaining the difference between the preformed cracks 26 and the emboss previously applied in the water pressure transfer sheet, the preformed cracks 26 serve as a component factor which determines the formation action of the swelling expansion cracks in the early stage where the water pressure transfer sheet lands on the water and the subsequent swelling expansion cracks develop and advance from the initial action while the emboss never acts effectively to control the formation action of the swelling expansion cracks in early stages where the water pressure transfer lands on the water like the preformed cracks 26. Thus, it should be understood that the emboss cannot have the same function as the preformed cracks 26.

(Followability of the Non-Extensible Decorative Layer to the Article)

As already stated, the non-extensible decorative layer 22 such as the metal layer 22M imparting the hologram function cannot originally follow the three-dimensional surface of the article due to the non-extensibility at the time of the water pressure transfer, but the swelling expansion cracks are produced in the non-extensible decorative layer 22 following the swelling expansion of the water-soluble base substance film 20B according to the thickness of the non-extensible decorative layer 22 or the pitch and the depth, etc. of the emboss of the non-extensible decorative layer 22 at the time of the water pressure transfer and therefore the non-extensible decorative layer 22 can be followed on the surface of the article to some extent. However, since the swelling expansion cracks are spontaneously formed in the uneven and random mode which causes them to be not controlled, the followability of the non-extensible decorative layer to the surface of the article is unstable, which disadvantageously causes the followability to the article to be lowered. However, according to the method of the invention, since the preformed cracks 26 of the non-extensible decorative layer 22 are formed in a stable form under the controlled conditions before the water pressure transfer sheet 20 lands on the water (before the original step of the water pressure transfer), the stable extensibility accompanying the generation of the swelling expansion cracks in the non-extensible decorative layer 22 is imparted together with the swelling expansion of the water-soluble base substance film 20B at the time of the water pressure transfer and therefore, the water pressure transfer sheet 20 having the non-extensible decorative layer 22 may be attached onto the three-dimensional surface of the article in a stable manner with the high attachment followability while following the surface of the article. This may be true in case of having the extensible decorative layer 24 of FIG. 3.

(Permeation of the Activating Agent into the Extensible Decorative Layer or the Transparent Resin Layer)

As already stated, in case where the water pressure transfer sheet 20 has the dried extensible decorative layer 24 under the non-extensible decorative layer 22, in the conventional method, the activating agent required for imparting the extensibility to the extensible decorative layer 24 is prevented by the non-extensible decorative layer 22 from permeating into the extensible decorative layer 24 whereby the extensible decorative layer 24 cannot extend and therefore, the water pressure transfer sheet has the poor attachment followability thereof to the article at the time of water pressure transfer. Thus, the decoration of the article using the water pressure transfer sheet having the extensible decorative layer 24 under the non-extensible decorative layer 22 has been practically impossible. On the other hand, in the method of the invention, since the plurality of preformed cracks 26 are formed in the non-extensible decorative layer 22 laminated on the extensible decorative layer 24 on its upper side before the water pressure transfer sheet 20 lands on the water for water pressure transfer, the activating agent applied to the non-extensible decorative layer 22 of the water pressure transfer sheet 20 can permeate into the extensible decorative layer 24 through the preformed cracks 26 of the non-extensible decorative layer 22 and therefore, the extensibility of the extensible decorative layer 24 can be imparted thereto to improve the attachment followability thereof to the article at the time of the water pressure transfer. Thus, even if the water pressure transfer sheet 20 having the dried extensible decorative layer 24 under the non-extensible decorative layer 22 is used, both of the decorative layers 22 and 24 can be positively transferred under water pressure and therefore the performance of the decorated article in combination with its functionality and design property can be improved. Also, in case where the water pressure transfer sheet 20 has the dried transparent resin layer 22C under the non-extensible decorative layer 22, the transparent resin layer 22C can have the extensibility imparted thereto similarly by the permeation mechanism of the activating agent as above described. The activating agent permeating into the extensible decorative layer 24 through the preformed cracks 26 of the non-extensible decorative layer 22 also serves to restore the adhesiveness of the extensible decorative layer 24 to improve the adhesiveness of the extensible decorative layer 24 and the non-extensible decorative layer 22.

Although the preformed cracks 26 are required to penetrate in the thickness direction of the non-extensible decorative layer 22 in order for the activating agent to pass through the non-extensible decorative layer 22, all the preformed cracks 26 do not need to penetrate in the thickness direction of the non-extensible decorative layer, as long as there is no trouble in passage of the activating agent, some preformed cracks 26 penetrate through the decorative layer 22 and other preformed cracks 26 do not need to penetrate through the decorative layer 22. Even though depending on the formation means of the preformed cracks, it has been confirmed in the experiment that when actually forming the preformed cracks 26 in the non-extensible decorative layer 20, the preformed cracks 26 have both of the penetrating type and non-penetrating type mainly intermingled in the state of more penetrating type than not-penetrating type.

(A. Preformed Cracks)

(1) The Depth of the Preformed Cracks 26 Formed in the Non-Extensible Decorative Layer 22

The preformed cracks 26 should just be formed in the non-extensible decorative layer 22 in the thickness direction of the non-extensible decorative layer 22 to such an extent of the depth thereof that the swelling expansion cracks can be suitably formed in the non-extensible decorative layer 22 after the water pressure transfer sheet lands on the water and the cracks need not penetrate through the non-extensible decorative layer 22 (see FIG. 12(D)), but as already stated, in case of the water pressure transfer sheet having the extensible decorative layer 24 laminated under the non-extensible decorative layer 22 (on the side of the water-soluble base substance film), at least some preformed cracks 26 penetrate through the non-extensible decorative layer 22 in the thickness direction thereof in order that the activating agent can easily permeate through the extensible decorative layer 24 (see FIG. 12 (C)).

(2) Width of the Preformed Cracks 26

The width of the preformed cracks 26 is desirably as narrow as possible from the viewpoint of the design property after the water pressure transfer, it is desirably in a range of 0.1-1 micrometers. What is meant by the width of the preformed cracks is a distance between the shortest two points of the portions protruding on the surface of the non-extensible decorative layer 22.

(3) The Length of the Preformed Cracks 26

The length of the preformed cracks 26 is suitably set according to the pattern.

(B. Relation Between the Preformed Cracks and the Swelling Expansion Cracks)

How to advance in the formation of the swelling expansion cracks of the non-extensible decorative layer 22 by the application of the adhesives or the activating agent and by the swelling of the water-soluble base substance film after the water pressure transfer sheet lands on the water changes due to the form of the preformed cracks, more concretely due to the pattern of the preformed cracks and the quantity of the preformed cracks.

Generally, the cracks formed in a solid have constitution elements of primary cracks serving as chief components and secondary cracks formed by branching from the primary cracks in view of time order relation in the formation process. This is also true of the preformed cracks. The formation pattern of the preformed cracks comprises a form including only a plurality of primary cracks 60 (see FIG. 12 (A)) and a form in which a plurality of primary cracks 60 and a plurality of secondary cracks 61 are combined (see FIG. 12 (B)) and the expansion direction and the expansion speed of the water pressure transfer film after it lands on the water and the uniformity of the swelling expansion cracks can be adjusted according to the formation pattern form. Furthermore, more particularly, the form of the swelling expansion cracks may be adjusted by parameters (the number, the length, the form and other factors) of the primary and secondary cracks of the preformed cracks 26 and the distance (pitch) between the adjacent preformed cracks 26. Since the narrower the distance is, the more the number of the preformed cracks is, the swelling expansion cracks can be more easily formed at the time of water pressure transfer and the expansion speed becomes larger and therefore, the swelling expansion cracks can be formed much more uniformly and minutely and the attachment followability and the design property of the non-extensible decorative layer 22 at the time of water pressure transfer are improved. Since the expansion time per unit length of the non-extensible decorative layer 22 and the water-soluble base substance film 20B can be also adjusted according to the number of the preformed cracks 26, in the continuation type water pressure transfer as shown in FIG. 1, the expansion action of the water pressure transfer sheet can be adjusted so that it becomes the predetermined expansion rate in the set-up transfer position. Furthermore, the expansion direction can be also adjusted by changing the rate of the number of the primary crack to the secondary cracks of the preformed cracks 26. Since there is a case where the design property of the water pressure transfer article may change according to the formation processes of the swelling expansion cracks, the number of the preformed cracks per unit area is desirably in a range of 1000-2100/mm$^2$.

(Formation Conditions of the Preformed Cracks)

Since the expansion speed and the expansion direction of the water pressure transfer sheet 20 can be adjusted according to the form of the preformed cracks 26, in the case where the expansion rate of the water-soluble base substance film 20B of the water pressure transfer sheet 20 varies between the longitudinal direction and the transverse direction, for example, the preformed cracks 26 may be preferably formed along the direction where the expansion rate of the water-soluble base substance film 20B is larger so that the water pressure transfer sheet easily expands in the direction where the expansion rate is smaller when the water pressure transfer sheet expands due to the formation of the swelling extensibility cracks. More concretely, in the water pressure transfer sheet used for the continuation type water pressure transfer method, the preformed cracks 26 are formed in a slit-like form in parallel with the direction (the direction of arrow b of FIG. 10) perpendicular to the direction where the water pressure transfer sheet 20 is fed (the direction of an arrow a of FIG. 10), as shown in FIG. 10. This is why in case where the water-soluble base substance film 20B has high extensibility in its widthwise direction (the direction of arrow b), but has low extensibility in the feeding direction (the direction of arrow a), the formation and advance of the swelling extensibility cracks depend on the magnitude of the expansion force (stress) of the water-soluble film and therefore, it is required to heighten the extensibility of the water pressure transfer sheet 20 in the direction of arrow a where the extensibility of the water-soluble base substance film 20B is lower in order to promote the expansion of the non-extensible decorative layer 22 in the feeding direction (the direction of arrow a). The distance (pitch) of the preformed cracks 26 may be suitably set according to the quality and the thickness of the material of the non-extensible decorative layer 22 and the pitch and the depth of the emboss. Although the invention may be usually applied to the continuation type water pressure transfer method in which the water pressure transfer sheet 20 is fed out by a supply roll 20R from a source of supply 20S and lands on the water within a transfer tub 30 at the predetermined velocity whereby the water pressure transfer is sequentially carried out on a plurality of articles, as shown in FIG. 1, but it may be also applied to the batch type transfer system in which the water pressure transfer is carried out for every one article by using the water pressure transfer sheet 20 cut out to the size corresponding to the transfer face of the article and expanding it at the water-landing position after its landing within the transfer tub. In this case, since there is used the water pressure transfer sheet including the water-soluble base substance film having equal expansion rate in all the directions, the preformed cracks has no limitation of the expansion direction and they are just formed so that the non-extensible decorative layer 22 can expand uniformly in all the directions and therefore, the preformed cracks 26 may be preferably in the approximate lattice-like form of the primary and secondary cracks or in the form such as a radial form, a concentric circle form or a cobweb form rather than of the slit type. The cracks of these forms can be easily formed by stamping molding.

(Formation of the Preformed Cracks and Water Pressure Transfer)

Hereinafter, some forms of embodiment of the invention will be explained in detail with reference to FIGS. 4 through 9 based on the composition of the water pressure transfer sheet 20. The forms of embodiment of FIGS. 4 and 5 are those in which the preformed cracks 26 are formed in the non-extensible decorative layer 22 in the step where the water pressure transfer sheet 20 is fed out for the purpose of the water pressure transfer while the forms of embodiment of FIGS. 6 through 9 are those in which the preformed cracks 26 are previously formed in the non-extensible decorative layer 22 of the water pressure transfer sheet 20.

Figure 4:
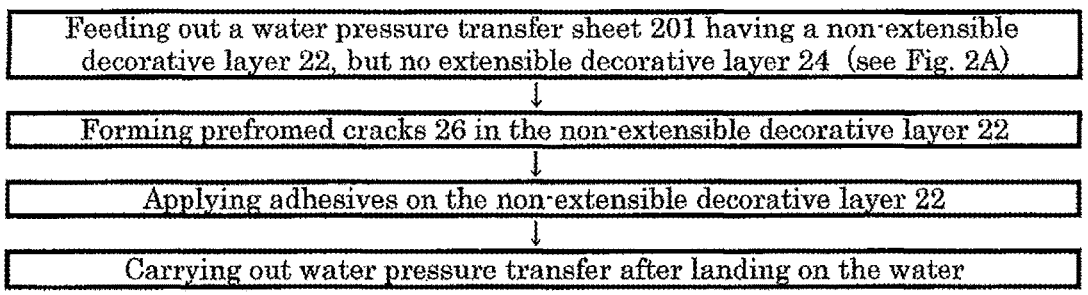
FIG. 4 is a flow chart of the water pressure transfer method in a first form of embodiment of the invention.

FIG. 4 shows the water pressure transfer method according to the first form of embodiment of the invention and this first form of embodiment is that in which the water pressure transfer is carried out using the water pressure transfer sheet 201 having the non-extensible decorative layer 22 as shown in FIG. 2 (A), but having no extensible decorative layer 24. In this first mode of embodiment, the water pressure transfer is carried out in which many preformed cracks 26 are formed in the non-extensible decorative layer 22 of the water pressure transfer sheet 201 before the water pressure transfer sheet 201 lands on the water 30W (lands on the water) when it is fed out from the source of supply 20S toward the water pressure transfer step and adhesives are applied before the formation of the preformed cracks 26 or simultaneously therewith. FIG. 1(B) illustrates the state where the water pressure transfer is carried out according to this form and a reference numeral 40 designates a crack formation process, but the concrete method will be explained later.

Figure 5:
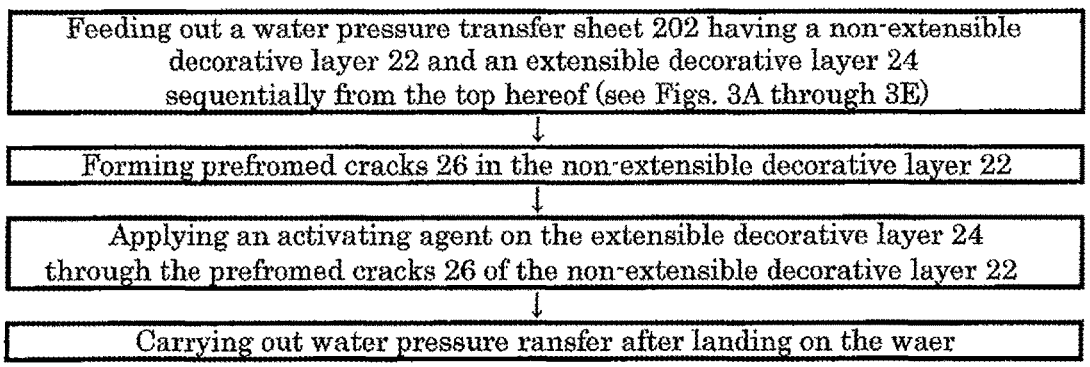
FIG. 5 is a flow chart of the water pressure transfer method in a second form of embodiment of the invention.

FIG. 5 shows the water pressure transfer method according to the second mode of embodiment of the invention and this second mode of embodiment is that in which the water pressure transfer is carried out by using the water pressure transfer sheet 202 having the non-extensible decorative layer 22 and the extensible decorative layer 24 sequentially from the top thereof as shown in FIGS. 3(A) through 3 (E). In the second mode of embodiment, firstly, many preformed cracks 26 are formed in the non-extensible decorative layer 22 of the water pressure transfer sheet 202 before the water pressure transfer sheet 202 lands on the water, then the activating agent for moistening and activating the extensible decorative layer 24 is applied thereon, thereafter it lands on the water and the water pressure transfer is carried out. FIG. 1 (C) illustrates the state where the water pressure transfer is carried out according to the second form and in this figure, a reference numeral 40 designates a preformed crack formation process while a reference numeral 50 designates an activating agent application process. These concrete processes will be explained later.

Figure 6:
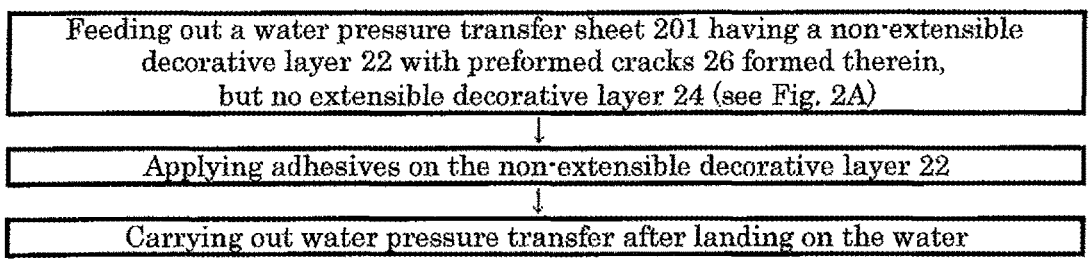
FIG. 6 is a flow chart of the water pressure transfer method in a third form of embodiment of the invention.

FIG. 6 shows the water pressure transfer method according to the third mode of embodiment of the invention and the third mode of embodiment is that in which the water pressure transfer is carried out by using the water pressure transfer sheet 201 comprising only the non-extensible decorative layer 22 having the preformed cracks 26 formed beforehand, as shown in FIG. 2(A). In the third mode, after applying adhesives on the water pressure transfer sheet 201, it lands on the water to thereby carry out the water pressure transfer. In the third mode of embodiment, the state where the water pressure transfer is carried out according to the third mode of embodiment is shown in FIG. 1 (A). Although the preformed cracks 26 are not shown in FIG. 2(A), the preformed cracks 26 are formed as shown in FIG. 12.

Figure 7:
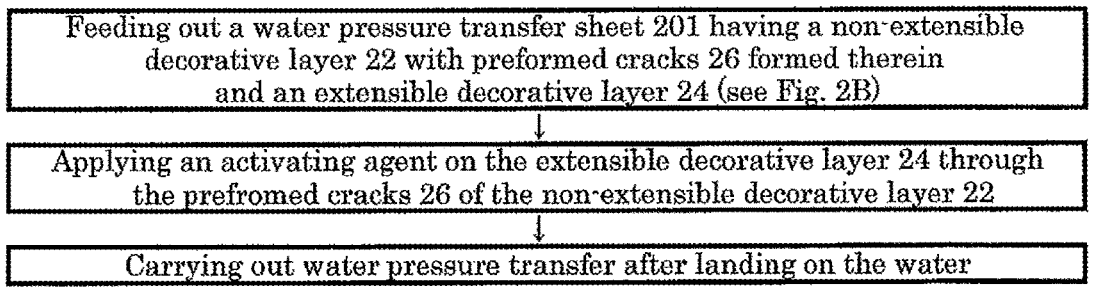
FIG. 7 is a flow chart of the water pressure transfer method in a fourth form of embodiment of the invention.

FIG. 7 shows the water pressure transfer method according to the fourth mode of embodiment of the invention and the fourth mode of embodiment is the form in which the water pressure transfer is carried out by using the water pressure transfer sheet 201 comprising the non-extensible decorative layer 22 having the preformed cracks 26 formed beforehand and the transparent resin layer 22C, as shown in FIG. 2 (B). In the fourth mode embodiment, after applying the activating agent on the water pressure transfer sheet 201, the water pressure transfer sheet lands on the water to carry out the water pressure transfer. The state of carrying out the water pressure transfer according to the fourth mode of embodiment is similarly shown in FIG. 1 (A). Similarly, although the preformed cracks 26 are not shown in FIG. 2(B), the preformed cracks 26 are formed as shown in FIG. 12. Although the transparent resin layer 22C may be under the non-extensible decorative layer 22, it may be in the upper side thereof.

Figure 8:
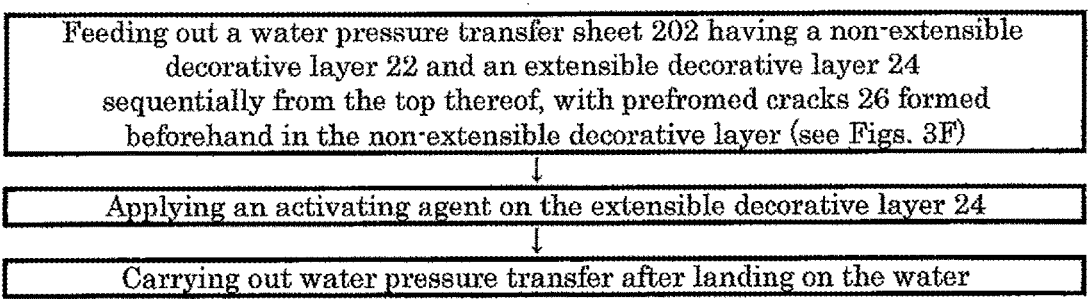
FIG. 8 is a flow chart of the water pressure transfer method in a fifth form of embodiment of the invention.

FIG. 8 shows the water pressure transfer method according to the fifth mode of embodiment of the invention and the fourth mode of embodiment is in the form where the water pressure transfer is carried out by using the water pressure transfer sheet 202 comprising the non-extensible decorative layer 22 having the preformed cracks 26 formed beforehand and the extensible decorative layer 24 sequentially from the top thereof as shown in FIGS. 3(A) through 3 (E). In the fifth mode of embodiment, after applying the activating agent on the water pressure transfer sheet 202, the water pressure transfer sheet 202 lands on the water to thereby carry out the water pressure transfer. Although the state where the water pressure transfer is carried out according to the fifth mode of embodiment is similarly shown in FIG. 1 (A) and although the preformed cracks 26 are not shown similarly in FIG. 3(A) through 3 (E), the preformed cracks 26 is formed as shown in FIG. 12.

Figure 9:
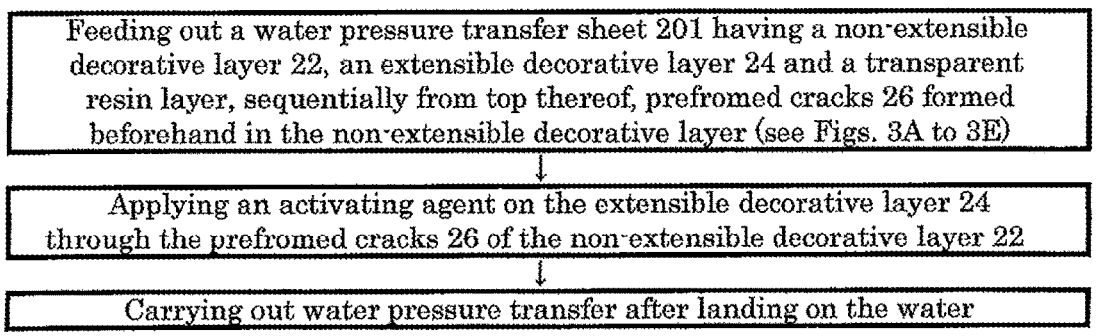
FIG. 9 is a flow chart of the water pressure transfer method in a sixth form of embodiment of the invention.

FIG. 9 shows the water pressure transfer method according to the sixth mode of embodiment of the invention and the sixth mode of embodiment has the form where the water pressure transfer is carried out using the water pressure transfer sheet 202 comprising the extensible decorative layer 24, the non-extensible decorative layer 22 having the preformed cracks 26 formed beforehand and the transparent resin layer 22C sequentially from the top of the water pressure transfer sheet 202 as shown in FIG. 3 (F). In the sixth mode of embodiment, after applying the activating agent on the extensible decorative layer 24 of the water pressure transfer sheet 202, the water pressure transfer sheet 202 lands on the water to thereby carry out the water pressure transfer. In this case, the activating agent applied to the extensible decorative layer 24 permeates the transparent resin layer 22C through the preformed cracks 26 of the non-extensible decorative layer 22 and the transparent resin layer 22C has the extensibility imparted thereto whereby all the layers 22, 22C and 24 to be transferred may be transferred with the good attachment followability without preventing the expansion extensibility of the water-soluble base substance film 20B. The state where the water pressure transfer is carried out according to the sixth mode of embodiment is also similarly shown in FIG. 1 (A) and similarly, although the preformed cracks 26 are not shown in FIG. 3 (F), the preformed cracks 26 may be formed as shown in FIG. 12.

The application of the activating agent in the second mode of embodiment and the fourth through sixth modes of embodiment may be performed before the formation of the preformed cracks 26 or simultaneously with the formation of the preformed cracks. In the first and third modes of embodiment, when the adhesiveness between the surface of the water pressure transfer article and the non-extensible decorative layer is not required, the water pressure transfer may be carried out without applying the adhesives.

In the first through sixth modes of embodiment, the application of the adhesives or the activating agent may be performed not before the water pressure transfer sheet 20 lands on the water, but after it lands on the water The application of the adhesives or the activating agent after the water pressure transfer sheet 20 lands on the water may be preferably performed at the timing when the water-soluble base substance film 20B of the water pressure transfer sheet 20 starts swelling after it lands on the water. In case where the adhesives or the activating agent are applied after the water pressure transfer sheet 20 lands on the water, the application process of spraying system may be desirably used.

(Adhesives or Activating Agent)

The well-known activating agent composite currently used for the conventional water pressure transfer may be used as the activating agent for activating the extensible decorative layer 24 or the transparent resin layer 22C. A solvent type activating agent is a solvent type composite comprising a resin component, a solvent and a plasticizer as an essential ingredient, for example, which may further include particulate silica. Since the adhesives for imparting the adhesiveness to the non-extensible decorative layer 22 may contain an adhesive ingredient in the component of the solvent type activating agent for activating the extensible decorative layer 24, the same solvent type activating agent may be used but the ingredient different from the activating agent may be used. In case where the top layer is the extensible decorative layer 24 (see FIG. 3F), the extensible decorative layer 24 is adhered to the surface of article 10 by the adhesiveness restored by the activating agent applied thereon, but in case where the top layer is the non-extensible decorative layer 22 (see FIG. 2, FIGS. 3A through 3E), the activating agent applied thereon permeates the extensible decorative layer 24 and the transparent resin layer 22C positioned thereunder through the preformed cracks 26 and in addition thereto, the non-extensible decorative layer 22 may be adhered to the surface of article 10 by the adhesive ingredient in the adhesives or the activating agent which remains in the non-extensible decorative layer 22, which should be understood.

(Formation of the Preformed Cracks)

The preformed cracks formation process 40 of FIGS. 1 (B) and 1(C) may be performed by using a method of forming the preformed cracks 26 in which tensile stress is applied in the direction along the surface of the water pressure transfer sheet 20 to the non-extensible decorative layer 22 by means (A) to extend the non-extensible decorative layer 22 to generate cracks, ridge means (B) such as tooth type stamping, roll with tooth or polygonal roll or other suitable means.

Examples of means (A) to apply tensile stress to the water pressure transfer sheet 20 to elongate the non-extending decorative layer include;

(A1) a method of providing one or more guide rolls between the source of supply 20S and the supply roll 20R for the water pressure transfer sheet 20 to contact the guide rolls so as to be nonlinearly guided and applying a tensile and bending stress to the water pressure transfer sheet so that the water pressure transfer sheet may be forced against the contact surface of the guide roll or rolls (A2) a method of providing one or more guide rolls for guiding the water pressure transfer sheet 20 to be displaced forwardly or rearwardly relative to the direction where the water pressure transfer sheet 20 is reversed by the guide roll or rolls to thereby apply tensile and bending stress to the water pressure transfer sheet so that the water pressure transfer sheet may be forced against the contact surface of the guide roll or rolls In these methods, the distance (pitch) of the preformed cracks 26 may be adjusted by the curvature of the guide roll or rolls and the magnitude of the stress.

The tooth type or polygonal type roll (ridge) means (B) may comprise a tooth type or polygonal type roll(s) (ridge) serving also as the supply roll of FIG. 1 and such roll or rolls may have the function of the preformed crack formation as well as the function of supply of the water pressure transfer sheet.

In the means to extend the non-extensible decorative layer 22, the rate of extension of the water pressure transfer sheet 20 increases according to the magnitude of tensile stress of the water pressure transfer sheet 20, the rate of increase in the extension changes also according to the thickness of the non-extensible decorative layer and therefore, the tensile stress may be set according to the thickness of the non-extensible decorative layer. The percentage of increases of the length of the extended non-extensible decorative layer relative to the length of the not-extended non-extensible decorative layer may be desirably 1 to 10% and more desirably 2 to 6%. In case where the decorative layers comprise the extensible decorative layer 24 and the non-extensible decorative layer 22, they have to be extended in the range where the design of the extensible decorative layer 24 is never effected. In case where the preformed cracks 26 are formed beforehand in the course in which the water pressure transfer sheet is manufactured, the methods identical to the aforementioned methods may be applied thereto.

(The Formation Conditions of Cracks and the Extensibility of the Water Pressure Transfer Sheet)

Figure 11:
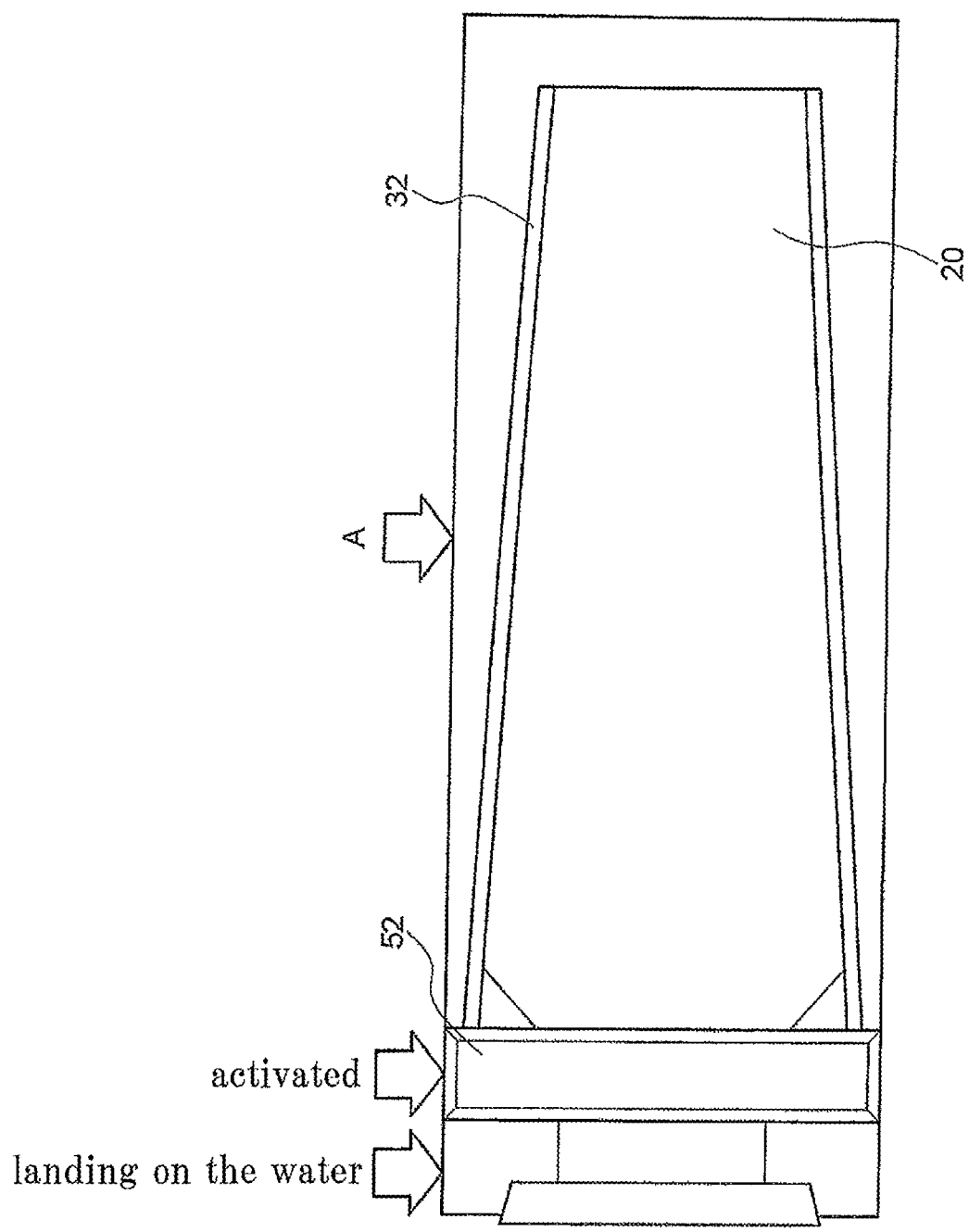
FIG. 11 is a plane view showing the step of activating the water pressure transfer sheet after it lands on water surface and narrowing the width of the water pressure transfer sheet in the method of the invention.

Since the smaller the pitch of the preformed cracks are and the more the number of the preformed cracks are, the extensibility is improved for the attachment followability to be better at the time of the water pressure transfer, the design property is improved, but in the continuation type water pressure transfer system, as illustrated in FIG. 11 (Note: the water pressure transfer sheet 20 advances from the left side to the right side), the water pressure transfer sheet 20 is defined in the widthwise direction by guide chains 32 within the transfer tub 30 and therefore, in case where the water pressure transfer sheet is fed on the conditions where the water pressure transfer sheet 20 contacts the guide chains 32 before the expansion of the water pressure transfer sheet 20 reaches the maximum value (saturation), the extension of the water pressure transfer sheet continues after it contacts the guide chains and therefore sometimes wrinkles may occur in the water pressure transfer sheet 20. The formation of the swelling expansion cracks of the non-extensible decorative layer 22 which will contribute to the expansion of the water pressure transfer sheet 20 after it lands on the water progresses having a balance with the resistance of the non-extensible decorative layer relative to the swelling stress of the water-soluble base substance film 20B. Thus, when the water pressure transfer is performed in the state where the expansion of the water pressure transfer sheet 20 is saturated, the more stabilized attachment followability may be realized, but since the delicacy of the transferred design becomes lower, there is sometimes a reciprocity relation between the stable attachment followability and the delicacy of the design. In these cases, it is preferable that after the water pressure transfer sheet 20 is completely extended (to the state where the expansion terminates, namely the expansion force disappears), the water pressure transfer may be performed in the state where the extension rate of the water pressure transfer sheet 20 is adjusted to the predetermined value by gradually narrowing the width of the extended water pressure transfer sheet 20 by the regulation means such as the guide chains 32 in the area (transfer area) A where the water pressure transfer is practically performed on the article so that the extension rate of the water pressure transfer sheet 20 reaches the predetermined value. The rate at which the width of the water pressure transfer sheet 20 is narrowed from the state where the water pressure transfer sheet 20 is most extended may be preferably 1 to 20% relative to the most extended width and more preferably 5 to 10% whereby the generation of the wrinkles at the time of expansion of the water pressure transfer sheet 20 can be avoided and therefore, the attachment followability at the time of transfer and the delicacy of the design of the transfer article may be compatible.

Although the activating agent application step 50 may be carried out by a roll coating system, a spray application system and other appropriate systems, which are conventionally used, FIG. 11 illustrates that the activating agent may be applied after the water pressure transfer sheet lands on the water by reciprocating type spray application apparatus 52.

In this manner, since the plurality of the preformed cracks 26 formed beforehand (intentionally) in the non-extensible decorative layer 22 of the water pressure transfer sheet 20 before the water pressure transfer sheet 20 lands on the water may be formed on the conditions suitably controlled at time when the water pressure transfer sheet is manufactured or in the step before the water pressure transfer lands on the water, the extensibility of the non-extensible decorative layer 22 (the formation action of the swelling expansion cracks) can be adjusted on the basis of the preformed cracks 26 by the swelling extension of the water-soluble base substance film 20B, and therefore, the decorated article having the followability of the decorative layers to the surface of the article (the attachment followability) and the functionality of the decorative layers stabilized can be obtained with high productivity.

In case where the water pressure transfer sheet 20 has the extensible decorative layer 24 (the print layer 24P, for example) and/or the transparent resin layer 22C in a dry state under the non-extensible decorative layer 22, since the activating agent permeates the extensible decorative layer 24 and/or the transparent resin layer 22C through the preformed cracks 26 beforehand formed in the non-extensible decorative layer 22 before its application to activate the decorative layer 24 and the resin layer 22C, the extensibility of the extensible decorative layer 24 and/or the transparent resin layer 22C is never prevented and therefore, the permeation of the activating imparts the stable extensibility to the whole water pressure transfer sheet 20 after it lands on the water together with the swelling of the water-soluble base substance film 20B, the swelling expansion cracks of the non-extensible decorative layer 22 and the preformed cracks 26. Thus, the good attachment followability of the decorative layers 22 and 24 and the resin layer 22C can be obtained with the result that the decorated article having the excellent functional design can be obtained in a stable manner.

Embodiment

Hereinafter, concrete EMBODIMENTS 1 through 10 (Table 1 to 2) of the invention will be explained in comparison with COMPARISONS 1 to 5.

TABLE 1

| | | | Embodiment 1 | Embodiment 2 | Embodiment 3 | Embodiment 4 | Embodiment 5 |
|---|---|---|---|---|---|---|---|
| Water pressure transfer sheet | Non-extensible decorative layer | Component | Al | Al | Al | Al | Al |
| | | Thickness [nm] | 30 | 30 | 30 | 30 | 40 |
| | Extensible decorative layer (presence) | | Yes | Yes | Yes | Yes | Yes |
| | Transparent resin layer (presence) | | — | — | — | — | — |
| | Preformed cracks | Form | I | I | I | I | I |
| | | Number/mm$^2$ | 544 | 754 | 1526 | 2018 | 1228 |
| | | Embossed | — | — | — | — | — |
| Evaluation | Expansion time in widthwise direction (sec) | | 48 | 44 | 32 | 20 | 32 |
| | Attachment followability | | ◎ | ◎ | ◎ | ◎ | ◎ |
| | Appearance of transfer article (Design property) | | ○ | ○ | ○ | ○ | ○ |

TABLE 2

| | | | Embodiment 6 | Embodiment 7 | Embodiment 8 | Embodiment 9 | Embodiment 10 |
|---|---|---|---|---|---|---|---|
| Water pressure transfer sheet | Non-extensible decorative layer | Component | Al | Al | TiO$_3$ | Al | TiO$_3$ |
| | | Thickness [nm] | 30 | 30 | 30 | 30 | 40 |
| | Extensible decorative layer (presence) | | Yes | — | Yes | Yes | Yes |
| | Transparent resin layer (presence) | | — | Yes | — | — | — |
| | Preformed cracks | Form | I | I | I | I | I |
| | | Number/mm$^2$ | 1596 | 1508 | 2003 | 1821 | 2015 |
| | | Embossed | — | — | — | Yes | Yes |

TABLE 2-continued

|  |  | Embodiment 6 | Embodiment 7 | Embodiment 8 | Embodiment 9 | Embodiment 10 |
|---|---|---|---|---|---|---|
| Evaluation | Expansion time in widthwise direction (sec) | 28 | 40 | 24 | 20 | 14 |
|  | Attachment followability | ◎ | ◎ | ◎ | ◎ | ◎ |
|  | Appearance of transfer article (Design property) | ○ | ○ | ○ | ○ | ○ |

TABLE 3

|  |  |  | Comparison 1 | Comparison 2 | Comparison 3 | Comparison 4 | Comparison 5 |
|---|---|---|---|---|---|---|---|
| Water pressure transfer sheet | Non-extensible decorative layer | Component | Al | Al | $TiO_3$ | Al | $TiO_3$ |
|  |  | Thickness [nm] | 30 | 30 | 30 | 30 | 40 |
|  | Extensible decorative layer (presence) |  | Yes | — | Yes | Yes | Yes |
|  | Transparent resin layer (presence) |  | — | Yes | — | — | — |
|  | Preformed cracks |  | — | — | — | — | — |
|  | Embossed |  | — | — | — | Yes | Yes |
| Evaluation | Expansion time in widthwise direction (sec) |  | Not expanded | Not expanded | Not expanded | Not expanded | Not expanded |
|  | Attachment followability |  | X | X | X | X | X |
|  | Appearance of transfer article (Design property) |  | X | X | X | X | X |

The water pressure transfer was performed onto a pattern-transferred body by the continuation type water pressure transfer method as shown in FIG. 1 while using the water pressure transfer sheets of the Embodiments 1 to 10 (Tables 1 and 2) and the Comparisons 1 to 4 (Table 3), respectively, the water-soluble base substance film 20B was removed by washing with water and thereafter the pattern-transferred body was dried to obtain the water pressure transfer article. The activating agent or the adhesives used was CPA-H DMP manufactured by Ohashi Chemical Industries Ltd. (solvent type) and it was sprayed and coated using a spray apparatus with the spraying amount of 10 g/m² immediately after the water pressure transfer sheet lands on the water, as shown in FIG. 11. In Table 1 and 2, "Forms I and II and the number of cracks" will be explained in detail later.

(Water Pressure Transfer Sheet of Embodiments 1 to 4)

The water pressure transfer sheets according to EMBODIMENTS 1 to 4 were prepared as follows.

There was prepared the water pressure transfer sheet by forming an aluminum (Al) vapor deposition film (non-extensible decorative layer) with a thickness of 30 nm using vapor deposition apparatus onto all over a print layer (extensible decorative layer) of "BLACK SHELL" (brand name of Taica Corporation, the applicant) having the pattern of woodgrain formed on a PVA film, which Taica Corporation have supplied to Taica's licensees. Subsequently, by pulling the water pressure transfer sheet in the longitudinal direction (corresponding to the direction of flow of water stream within the water pressure transfer tub) of the water-soluble film so that the increase percentage of the water pressure transfer sheet due to its pulling relative to the original length was in a range of 3 to 5%, the plurality of preformed cracks (the form I of FIG. 12 (A)) were formed in the widthwise direction (the direction perpendicular to the lengthwise direction) in the non-extensible decorative layer. The number of the preformed cracks of the non-extensible decorative layer was set to the number different for everyone of EMBODIMENTS 1 to 4 as shown in Table 1.

(Water Pressure Transfer Sheet of Embodiment 5)

The water pressure transfer sheet of EMBODIMENT 5 was identical to the water pressure transfer of EMBODIMENT 3 except that the thickness of the vapor deposition film was 40 nm and that the number of the preformed cracks differed a little from that of EMBODIMENT 3.

(Water Pressure Transfer Sheet of Embodiment 6)

The water pressure transfer sheet of EMBODIMENT 6 was identical to the water pressure transfer sheet of EMBODIMENT 3 except that the preformed cracks (form II of FIG. 12 (B)) was formed along both of the lengthwise and widthwise directions of the water-soluble film by pulling the water pressure transfer sheet in both directions and that the number of the preformed cracks differed a little from that of EMBODIMENT 3.

(Water Pressure Transfer Sheet of Embodiment 7)

The water pressure transfer sheet of EMBODIMENT 7 was identical to that of EMBODIMENT 3 except that an aluminum (Al) vapor deposition film (the non-extensible decorative layer) of 30 nm thickness on a transparent resin layer of 2 micrometer formed by applying a transparent ink (PCNT S medium C manufactured by Ibyo Ink, Inc.) of nitroglycerine cellulose system onto the water-soluble base substance film of polyvinyl alcohol (TS-40 manufactured by Aicello Corporation), that it had no extensible decorative layer and that the number of the preformed cracks differed a little from that of EMBODIMENT 3.

(Water Pressure Transfer Sheet of Embodiment 8)

The water pressure transfer sheet of EMBODIMENT 8 was identical to that of EMBODIMENT 4 except that the vapor deposition film was titanium oxide ($TiO_2$) and that the number of the preformed cracks differed a little from that of EMBODIMENT 4.

(Water Pressure Transfer Sheets of Embodiments 9 and 10)

The water pressure transfer sheets of EMBODIMENTS 9 and 10 were identical to those of EMBODIMENTS 3 and 8, respectively except that before forming the non-extensible decorative layer of vapor deposition film, the print layer of the extensible decorative layer was embossed (the pitch of 1 micrometer, the stripe pattern of depth of 0.05 to 0.3) by stamping and that the number of the preformed cracks of the non-extensible decorative layer differed a little from those of EMBODIMENTS 3 and 8, respectively.

(Water Pressure Transfer Sheet of Comparisons 1 to 3)

The water pressure transfer sheets of COMPARISONS 1 to 3 were identical to those of EMBODIMENTS 6 to 8 except that the non-extensible decorative layers had no preformed cracks formed.

(Water Pressure Transfer Sheets of Comparisons 4 and 6)

The water pressure transfer sheets of COMPARISONS 4 and 5 were identical to those of EMBODIMENTS 9 and 10, respectively except that the non-extensible decorative layers had no preformed cracks formed.

(The Form of Preformed Cracks)

The form of the preformed cracks was classified as follows.

Form I: There are main primary cracks and fewer secondary cracks.

Form II: There are primary and secondary cracks.

(The Number of Preformed Cracks)

The number of the preformed cracks was set to be the average of addition values of the number of the preformed cracks at arbitrary 10 places of the water pressure transfer sheet, which was obtained by visually counting the number of the cracks within the image area (0.056 mm$^2$) expanded by 1000 times with a microscope and converting the accounted number was converted into 1 mm$^2$. It was visually confirmed that the preformed cracks partially penetrate the decorative layer. Although it was difficult to carry out the directly visual confirmation of the penetration state of cracks, if the colored activating agent (or solvent) might be applied on the water pressure transfer sheet, then the visual confirmation of the penetration status of the activating agent (namely, the penetration status of the cracks) might be carried out from the side of the water-soluble base substance film 20B.

How to judge each characteristic of "evaluation" in Table 1 and 2 is as follows.

(Expansion Time)

The "expansion time" was a measurement time obtained by measuring with a stopwatch a time from the point of time when the completion of the application of the activating agent immediately after the water pressure transfer sheet landed on the water until the water pressure transfer sheet reached either of a pair of the guide chains on the both sides of the water pressure transfer tub. The distance between the pair of guide chains was 750 mm.

(Attachment Followability: Cylinder Test)

A cylinder test was the test in which to the curved surface of the pattern-transferred body of cylindrical test piece was transferred the print layer of the water pressure transfer sheet under liquid pressure along the axial direction and the attachment followability of the ink on the surface of this test piece was confirmed. Since the pattern-transferred body was cylindrical, the pattern changed according to the considerable modification stress when the water pressure transfer was carried out and the degree of the modification stress and its scale (area or range) changed according to the characteristic of the ink. Thus, the characteristic of the ink could be judged from the change of the pattern (the attachment followability of the ink). The test piece was a cylindrical body of cardboard of 30 mm in diameter (outer diameter) and of 200 mm in length ("TOCHIMAN first Kent paper F160" TOCHIMAN is a registered tradename). Together with the water pressure transfer sheet having the print pattern layer on which the activating agent was applied to recover its adhesiveness and floating on the water surface, the cylindrical body sunk underwater from one of the ends of the cylinder body at the velocity of 1.5 m/min with the axis and the transfer surface of the cylindrical body substantially perpendicular to each other whereby the print layer was transferred onto the cylindrical circumference. With the transfer starting position set at 0 mm, the case where the pattern was transferred all over the length of 200 mm from the transfer starting point without any collapse in the pattern was evaluated as "@" (double circle) (excellent), the case where the pattern was transferred with the collapse of the pattern in the range of 100 to 200 mm from the transfer starting point was evaluated as "◯" (circle) (good) and the case where the pattern was transferred with the collapse in the length less than 100 mm from the transfer starting point or not transferred was evaluated as "X" (improper). In these cases, since the cylindrical body sank underwater while the activated water pressure transfer sheet floating on the water surface was put thereon, the water pressure was applied on the water pressure transfer sheet (the side of the cylindrical body) put on the cylindrical body from the point of time when sunk underwater whereby the pattern is transferred on the side of the cylindrical body.

(Appearance: Design Property)

The transfer decoration state of the water pressure transfer article comprising a board of ABS material (TM 20 manufactured by MG ABS, Inc. was visually observed wherein the good state was evaluated as "◯" and the state where there was any collapse of the pattern or a portion not transferred was evaluated as "X" (improper).

(Result of Evaluation)

Although the evaluation of EMBODIMENTS and COMPARISONS is as described on the columns of "EVALUATION" in TABLES 1 and 2, the followings will be understood from the evaluation results.

(1) From comparison between EMBODIMENTS 1 to 4 and COMPARISON 1 and between EMBODIMENT 8 and COMPARISON 3, the attachment followability of EMBODIMENTS in which the plurality of the preformed cracks were formed in the vapor deposition film of the non-extensible decorative layer before the water pressure transfer sheet landed on the water was considerably improved as compared with COMPARISONS in which the preformed cracks were not formed and it is noted that in EMBODIMENTS, the water pressure transfer article having the excellent design property was obtained. This is because the extensible decorative layer could be expanded by at least parts of the preformed cracks penetrating in the thickness direction of the vapor deposition film and the activating agent permeating the extensible decorative layer through the penetration portions of the preformed cracks. The reason why the water pressure transfer sheets of COMPARISONS 1 and 3 through 5 could not be expanded at the time of transfer is that the extensible decorative layer was prevented from being wetted because the activating agent was prevented by the vapor deposition film from permeating the extensible decorative layer.

(2) From the comparison between EMBODIMENT 7 and COMPARISON 2, it will be noted that although the water pressure transfer sheet extended with the extension of the transparent resin layer, in EMBODIMENT 7 in which the plurality of preformed cracks were formed in the vapor deposition film of the non-extensible decorative layer before the water pressure transfer sheet landed on the water, the attachment followability was considerably improved as compared with COMPARISON 2 in which the preformed cracks were not formed.

Figure 13:
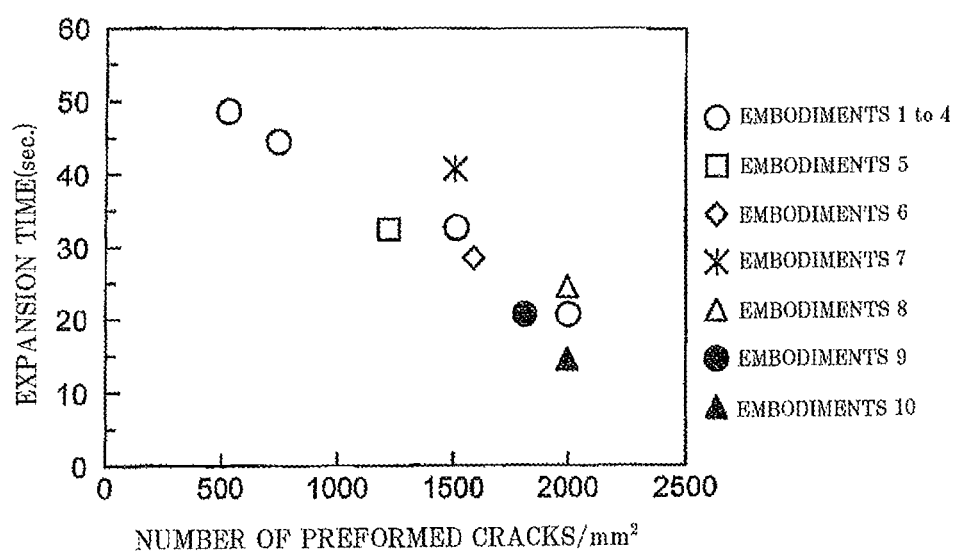
FIG. 13 is a distribution view showing the plotted correlation between the number of preformed cracks formed in the non-extensible decorative layer of the water pressure transfer sheet and the expansion time of the water pressure transfer sheet after it lands on water surface of a transfer tub regarding the first through tenth forms of embodiment of Table Nos. 1 and 2.

(3) FIG. 13 shows the result in case where there is plotted the relation between the number of the preformed cracks formed in the non-extensible decorative layer and the expansion time of the water pressure transfer sheet after it landed on the water in EMBODIMENTS 1 to 10. From this figure, it will be noted that there is a correlation in which the more the number of the preformed cracks were, the larger the extensibility of the water pressure transfer sheet became whereby the expansion time became shorter in spite of the composition of the water pressure transfer sheet. Thus, the extensibility of water pressure transfer sheet can be adjusted according to the conditions of the pattern (the form and the number) of the preformed cracks formed in the non-extensible decorative layer.

(4) From the result of EMBODIMENT 8, it will be noted that even though the quality of the material of the non-extensible decorative layer was not a metal alone, but a metal oxide, the good effect of the invention could be obtained in a manner similar to other EMBODIMENTS.

(5) From the result of COMPARISONS 4 and 5, it will be noted that if the plurality of preformed cracks were not formed even though the non-extensible decorative layer was embossed, the expansion of the water pressure transfer sheet hardly occurred at the time of water pressure transfer and therefore the good effect like those of EMBODIMENTS could not be obtained.

All the modes of embodiment of the invention and EMBODIMENTS are illustrated by way of example and the invention is not limited to those and might be embodied with other various modification and change. Therefore, the range of the invention is defined only by the attached claims and their equivalence.

INDUSTRIAL AVAILABILITY

According to the water pressure transfer method of the invention, the non-extensible decorative layer can be expanded in a stabilized manner by the preformed cracks formed in a controlled manner, in case where there is the dried extensible decorative layer under the non-extensible decorative layer, the activating agent permeates the extensible decorative layer through the preformed cracks of the non-extensible decorative layer and therefore the dried extensible decorative layer can be positively wetted. Thus, in either of the cases, the decoration article having the attachment followability and the design property improved can be obtained with high industrial availability.

EXPLANATION OF REFERENCE NUMERAL

10 Article
20, 201, 202 Water pressure transfer sheet
20B Water-soluble base substance film (carrier film)
20S Source of supply
20R Supply roll
20T Transfer layer tub
22 Non-Extensible decorative layer
22M Metal layer (or vapor deposition layer)
22C Transparent resin layer
24 Extensible decorative layer
24P Print layer
26 Preformed cracks
30 Water Pressure Transfer Tub
30W Water
32 Guide Chain
40 Crack Formation Step
50 Activating agent application step
52 Reciprocating spray coating apparatus
60 Primary cracks
61 Secondary cracks

The invention claimed is:

1. Water pressure transfer method comprising the steps of disposing, on water surface of a water pressure transfer tub, a water pressure transfer sheet comprising a water-soluble base substrate film and a transfer layer including at least a non-extendable decorative layer formed on said water-soluble base substrate film and forcing an article against said water pressure transfer sheet whereby said transfer layer is transferred onto a surface of said article, characterized in that said non-extendable decorative layer of said water pressure transfer sheet has a plurality of preformed cracks in the direction of thickness before said water pressure transfer sheet lands on said water surface, at least parts of said preformed cracks extend through said non-extendable decorative layer in the direction of thickness.

2. Water pressure transfer method as set forth in claim 1, and wherein in case where the expansion rates at the time of swelling of said water-soluble base substrate film of said water pressure transfer sheet vary based on the orthogonal directions of the water pressure transfer sheet, respectively, said plurality of preformed cracks are formed along the direction of larger expansion rate.

3. Water pressure transfer method as set forth in claim 2, and wherein in case where the water pressure transfer method is in the form of continuous water pressure transfer using the water pressure transfer sheet having the expansion rate of widthwise direction larger than that of the longitudinal (advancing) direction, said plurality of preformed cracks are formed along the widthwise direction of said water-soluble base substrate film.

4. Water pressure transfer method as set forth in claim 1, and wherein in case where said transfer layer includes an extensible decorative layer, said plurality of preformed cracks are formed before an activating agent is applied onto said water pressure transfer sheet.

5. Water pressure transfer method as set forth in claim 4, and wherein said plurality of preformed cracks are formed in advance at the manufacturing of said water pressure transfer sheet.

6. Water pressure transfer method as set forth in claim 1, and wherein in case where said water pressure transfer sheet includes only non-extensible decorative layer, said plurality of preformed cracks are formed before adhesives are applied onto said water pressure transfer sheet.

7. Water pressure transfer method as set forth in claim 6, and wherein said plurality of preformed cracks are formed in advance at the time of manufacture of said water pressure transfer sheet.

8. Water pressure transfer method as set forth in claim 1, and wherein said plurality of preformed cracks are formed before said water pressure transfer sheet is fed out from a source of supply and lands on the water and said water pressure transfer sheet is transferred underwater after it lands on the water.

9. Water pressure transfer method as set forth in claim 1, and wherein said water pressure transfer method is carried out by extending said water pressure transfer sheet to a state where the extension force disappears and thereafter gradually and forcibly reducing said water pressure transfer sheet in the widthwise direction until it becomes the state of predetermined reduced width.

10. Water pressure transfer method as set forth in claim 1, and wherein said non-extensible decorative layer is a metal layer or a metal oxide layer.

11. Water pressure transfer method as set forth in claim 10, and wherein at least the non-extensible decorative layer is embossed.

12. Water pressure transfer method as set forth in claim 4, and wherein said activating agent is applied at the time when said water pressure transfer sheet lands on the water surface and the water-soluble base substance film begins to swell.

13. Water pressure transfer sheet having a transfer layer including a water-soluble base substance film and at least a non-extensible decorative layer formed on said water-soluble base substance film, characterized in that said non-extensible decorative layer has a plurality of preformed cracks in the direction of thickness and wherein at least parts of said plurality of preformed cracks extend through the nonextensible decorative layer in the thickness direction thereof.

14. Water pressure transfer sheet as set forth in claim 13, and wherein said water pressure transfer sheet has expansion rates different on its orthogonal directions at the time of swelling, respectively and said plurality of preformed cracks are formed along the direction in which the expansion rate is larger.

15. Water pressure transfer sheet as set forth in claim 14, and wherein said plurality of preformed cracks are formed along the widthwise direction of said water pressure transfer sheet in case where the expansion rate of the widthwise direction of said water pressure transfer sheet is larger than the expansion rate of the longitudinal direction (advancing direction) thereof.

16. Water pressure transfer sheet as set forth in claim 13, and further including a dried extensible print layer under said non-extensible decorative layer.

17. Water pressure transfer sheet as set forth in claim 13, and wherein said non-extensible decorative layer is a metal layer or a metal oxide layer.

18. Water pressure transfer sheet as set forth in claim 13, and wherein a least of said non-extensible decorative layer is embossed.

19. Water pressure transfer method as set forth in claim 6, and wherein said adhesives are applied at the time when said water pressure transfer sheet lands on the water surface and the water-soluble base substance film begins to swell.

* * * * *

UNITED STATES PATENT AND TRADEMARK OFFICE
CERTIFICATE OF CORRECTION

PATENT NO. : 10,632,777 B2
APPLICATION NO. : 15/531899
DATED : April 28, 2020
INVENTOR(S) : Wataru Ikeda et al.

Page 1 of 1

It is certified that error appears in the above-identified patent and that said Letters Patent is hereby corrected as shown below:

In the Specification

Column 6, Line 45, "120" should be --12C--.

Column 20, Line 48, "Ibyo" should be --Toyo--.

Column 21, Line 8, "6" should be --5--.

Column 22, Line 8, ""@"" should be --"◎"--.

In the Claims

Column 26, Line 16, being Line 2 of Claim 18, delete "a least of".

Signed and Sealed this
Seventh Day of July, 2020

Andrei Iancu
*Director of the United States Patent and Trademark Office*